US006972169B2

(12) United States Patent
Illman et al.

(10) Patent No.: US 6,972,169 B2
(45) Date of Patent: Dec. 6, 2005

(54) FUNGAL DEGRADATION AND BIOREMEDIATION SYSTEM FOR CCA-TREATED WOOD

(75) Inventors: Barbara L. Illman, Madison, WI (US); Vina W. Yang, Verona, WI (US); Leslie A. Ferge, Middleton, WI (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 527 days.

(21) Appl. No.: 10/273,912

(22) Filed: Oct. 18, 2002

(65) Prior Publication Data

US 2003/0129732 A1 Jul. 10, 2003

Related U.S. Application Data

(62) Division of application No. 09/540,841, filed on Mar. 31, 2000, now Pat. No. 6,495,134.

(51) Int. Cl.[7] .............................................. A01N 63/00
(52) U.S. Cl. .................. 435/1.1; 435/262.5; 435/254.1; 424/93.5
(58) Field of Search ........................... 435/254.1, 262.5; 424/93.5

(56) References Cited

PUBLICATIONS

Illman et al., "Fungal Degradation of wood treated with metal–based preservatives: 1. Fungal tolerance," Int'l Research Group on Wood Preservation, 26th Annual Mtg., Doc. No.: IRG/WP96–10163 (Guadeloupe, French West Indies, May 19–24, 1996.*
Yang, V.W., and Illman, B.L., "Optimum Growth Conditions for the Metal–Tolerant Wood Decay Fungus, Meruliporia incrassata TFFH294," Int'l Research Group on Wood Preservation: 30th Annual Mtg., Doc. No.: IRG/WP 99– (Rosenheim, Germany, Jun. 6–11, 1999). ☐☐.*

Yang, V.W., and Illman, B.L., "Growth Study of a Metal Tolerant Wood Decay Brown Rot Fungus, Meruliporia incrassata, TFFH294," SIM, 1999 Annual Mtg., Poster Abstract (Aug. 1–6, 1999). ☐☐.*

Yang, V.W., and Illman, B.L., "Optimum Growth Conditions for the Metal–Tolerant Wood Decay Fungus, Meruliporia incrassata TFFH294," Int'l Research Group on Wood Preservation: 30th Annual Mtg., Abstract (Rosenheim, Germany, Jun. 6–11, 1999). ☐☐.*

Stephan, et al., "Microbial conversion of wood treated with salt preservatives," Material und Organismen, 179–199 (1995).*

R–D Peek, et al., "Microbial Deomposition of Salt Treated Wood," Int'l Research Group on Wood Preservation, 2nd Int'l Symp., Doc. No.: IRG/WP93–50001, 313–326 (Cannes–Mandelieu, 1993). ☐☐.*

"Standard Method of Testing Wood Preservatives by Laboratory Soil–Block Cultures," American Wood Preserver's Assoc. Book of Standards, 243–253(1991).*

* cited by examiner

*Primary Examiner*—Irene Marx
(74) *Attorney, Agent, or Firm*—John F. Fado; Lesley E. Shaw; Janet I. Stockhauser

(57) ABSTRACT

A method for degrading and/or bioremediating waste wood containing chromated copper arsenate (CCA) using a fungal inoculum is disclosed. The fungal inoculum comprises of at least one CCA-tolerant fungi, a lignocellulosic substrate and a nutrient supplement. The fungal inoculum is applied to the waste wood and maintained in an aerated and hydrated environment having temperature conditions sufficient to allow the inoculum to grow and metabolize the CCA. The inoculum and the waste wood are combined until an end product that is at least partially remediated or of a reduced volume.

16 Claims, No Drawings

FUNGAL DEGRADATION AND BIOREMEDIATION SYSTEM FOR CCA-TREATED WOOD

CROSS-REFERENCE TO RELATED APPLICATIONS

This is a Divisional application of U.S. Ser. No. 09/540,841, filed Mar. 31, 2000, now U.S. Pat. No. 6,495,134.

STATEMENT REGARDING FEDERALLY SPONSORED RESEARCH OR DEVELOPMENT

BACKGROUND OF THE INVENTION

The present invention relates to fungal inocula and their use in degrading and bioremediating wood treated with chemical preservatives. More specifically, this invention discloses and claims a fungal inoculum, the method of its preparation, and its use in degrading and bioremediating wood treated with chromated copper arsenate.

Wood used in the construction of today's decks, docks and buildings, or as utility poles and railroad ties, is typically treated with a chemical preservative to prevent its deterioration and extend its service life. The chemical preservative used will generally depend upon the intended use of the wood and often includes chemicals such as chromated copper arsenate (CCA), ammoniacal copper quat (ACQ), creosote and pentachlorophenol. Of these preservatives, CCA is one of the most prevalent due to its minimal cost, and because it provides a dry and paintable surface after its application and leaves the wood relatively leach-resistant.

Treated wood is typically collected and stored at landfills or other facilities once it reaches the end of its useful life. Presently, large quantities of this waste wood is accumulating in landfills at an alarming rate. The collection and storage of such large quantities of waste wood in a single location creates an environment where the contamination of the surrounding soil and groundwater by toxic, environmentally-persistent chemicals is a likely result.

Contamination of soils and groundwater with toxic, environmentally-persistent chemicals is a serious problem. Toxic, environmentally-persistent chemicals are those that are resistant to degradation in the natural environment. As such, these chemicals pose a multi-faceted problem in that as they persist and accumulate in the environment, their toxicity, including in many instances, proven carcinogenicity, presents substantial health risks to both animals and human beings.

Environmental contamination from CCA-treated wood is specific concern in view of the large volume of CCA-treated waste wood expected to be removed from service and disposed of in the near future. Although CCA-treatment is considered to be highly leach resistant, small amounts of Cu, Cr and As contaminates are still measurable in leach water and soils.

The prior art is replete with methods for degrading hazardous chemicals. However, this prior art is generally, and specifically, directed towards halogenated aromatic compounds. Suggested treatment strategies include incineration of the waste, removal and isolation of the contaminated materials, and degradation of the pollutant by bacteria.

All of these strategies suffer from serious deficiencies. Incineration is extremely expensive due to the required energy expense and the necessity of moving the contaminated material to remote locations. Incineration is also impractical because of the large quantities of waste which needs processing. Removal and isolation of the contaminated material is also expensive and does nothing to effect a long-term solution. Degradation of the chemicals using bacteria has also proven ineffective due to the bacteria's specificity for particular chemicals and its sensitivity to the toxic chemicals and environmental conditions.

U.S. Pat. No. 5,476,788 employs another strategy which utilizes an inoculum containing lignin-degrading fungal species *Phanerochaete chrysosporium, Phanerochaete sordida,* or *Trametes hirsuta* to remediate solid materials, such as soils, sludge, sediments, and debris (e.g., woods), contaminated with pentachlorophenol. The inoculum contains one or more of the fungal strains and a lignocellulosic substrate, i.e., sawdust. In its use, the inoculum is combined with the pentachlorophenol-contaminated material and the entire mixture is aerated and hydrated until the inoculum metabolizes the pentachlorophenol to a less toxic product. Typically, this less toxic product includes pentachloroanisole.

Although the above-identified bioremediation strategy provides a useful means of reducing the pentachlorophenol content in various solid materials, it does not address the concerns associated with other wood preservatives currently used in the world today. Moreover, it fails to provide a working strategy for other types of fungal strains which require a more specific and unique environment to effectively remediate chemical preservatives such as CCA, ACQ, creosote, or pentachlorophenol or degrade wood treated with these chemicals.

BRIEF SUMMARY OF THE INVENTION

The present invention is summarized in that it discloses a fungal inoculum, the method of its preparation, and its use in degrading and/or bioremediating wood treated with the chemical preservative chromated copper arsenate (CCA).

The disclosed fungal inoculum generally comprises of at least one CCA-tolerant fungus, a lignocellulosic substrate, and a nutrient supplement. The CCA-tolerant fungal strains are preferably selected from the group consisting of *Meruliporia incrassata* (TFFH-294), *Antrodia radiculosa* (MJL-630), *Meruliporia incrassata* (Mad-563) and *Antrodia radiculosa* (FP-90848-T). The lignocellulosic substrate is preferably sawdust or wood chips. Other feasible substrates are rice straw, corn stalks, and wheat straw. The nutrient supplement is preferably selected from the group consisting of corn steep liquor, cornmeal and wheatbran.

In one preferred embodiment, the fungal inoculum is prepared by first growing the CCA-tolerant fungus in dark, aerobic conditions, having a relative humidity and a temperature sufficient to support fungal growth. The fungus is then combined with a homogenous matrix comprising sterile water, the nutrient supplement, and the sterilized lignocellulosic substrate, to form the fungal inoculum. The fungal inoculum is then allowed to mature by exposing the mixture to dark, aerobic conditions, at a relative humidity and in a temperature range sufficient to allow the fungus to reach a confluent growth.

Waste wood containing CCA is remediated or degraded by inoculating the waste wood in the fungal inoculum. To inoculate the waste wood, the fungal inoculum is first spread over the waste wood until all of the waste wood is covered. The waste wood and fungal inoculum mixture is then aerated and hydrated for a time and under conditions sufficient to allow the inoculum to at least partially remediate the CCA and/or degrade the waste wood to a desired degradation product. In some instances the degradation product may be capable of reuse in paper or wood composites, or simply have a reduced volume.

It is an object of the present invention to provide a method of bioremediating and/or degrading chemically treated waste wood to achieve a product having a reduced volume and/or the capacity to be reused as a wood fiber resource.

It is another object of the present invention to provide a fungal inoculum, and a method for preparing said fungal inoculum, which is useful in bioremediating and/or degrading chemically treated waste wood.

It is another object of the present invention to provide a fungal inoculum, and a method for using the fungal inoculum, to degrade and at least partially remediate waste wood chemically treated with CCA.

One advantage of the present invention is that the CCA-tolerant fungi utilized do not require genetic alteration to specifically grow in the presence of CCA. Thus, the introduction of the fungi into the environment provides no new, non-naturally occurring organisms.

Another advantage is that the preparation and use of the fungal inoculum is fairly simple and utilizes agricultural waste products and waste products from saw mills and urban chipping. These products have the additional advantage of providing a quick and low cost food source for the fungus, while having the added effect of stimulating rapid and extensive fungal growth, as well as providing a readily storable and transportable solid matrix.

Another advantage is that the inoculum and its method of use are particularly well suited for waste woods such as pressure-treated lumber from buildings, decks, utility poles and railroad ties. Specifically, the solid matrix of the fungal inoculum provides a wood environment for fungal growth which is similar to that of the waste wood. The fungal strain is, therefore, readily adapted to the waste wood environment upon inoculation and does not require a period of adjustment before degradation and bioremediation begins.

These and other objects and advantages of the invention are readily understood in view of the following detail description and examples.

DETAILED DESCRIPTION OF THE INVENTION

Waste wood containing chromated copper arsenate (CCA) is degraded and remediated in accordance with the present invention by inoculating the waste wood with a fungal inoculum comprising at least one CCA-tolerant fungus, a lignocellulosic substrate and a nutrient supplement. The fungal inoculum is applied to the waste wood and maintained in an aerated and hydrated environment having temperature conditions and a moisture content sufficient to allow the inoculum to grow and at least partially remediate the CCA or degrade the preservative treated wood. The inoculum and the waste wood are combined until a degradation product is achieved that is either of a volume consistent with the desires of the practitioner or capable of being recycled and used for paper or other composite woods.

CCA-tolerant fungi according to the present invention are generally defined as fungi capable of surviving and sustaining growth while being exposed to CCA. In the preferred embodiment, the CCA-tolerant fungi include, without limitation, *Meruliporia incrassata* (TFFH-294), *Antrodia radiculosa* (MJL-630), *Meruliporia incrassata* (Mad-563) and *Antrodia radiculosa* (FP-90848-T). Most preferably, the fungus utilized is *Meruliporia incrassata* (TFFH-294). The CCA-tolerant fungi, however, may also include any other CCA-tolerant fungus capable of degrading or bioremediating the treated waste wood. Preferably, the chosen fungus should provide a twenty percent (20%) or more dry weight loss in the waste wood after about ten weeks of reaction time.

In the preferred embodiment, the CCA-tolerant fungi are naturally existing fungi and not genetically altered or conditioned to grow under specific conditions or in the presence of a particular preservative. It is anticipated, however, that one skilled in the art may use a genetically altered or conditioned fungus in accordance with the present invention. Genetically altered or conditioned fungi may include, but are not limited to, any fungus modified to grow in the presence of a specific nutrient supplement or food source.

In accordance with the Budapest treaty, the strains *Meruliporia incrassata* (TFFH-294), *Antrodia radiculosa* (MJL-630), *Meruliporia incrassata* (Mad-563) and *Antrodia radiculosa* (FP-90848-T) were deposited with the Agricultural Research Culture Center (NRRL), an International Depositary Authority located at 1815 North University Street, Peoria, Ill. 610604 U.S.A., on Jul. 30, 1999, and given the accession numbers NRRL 30165, NRRL 30169, NRRL 30171, and NRRL 30166, respectively.

The lignocellulosic substrate serves as a long-term food source for the fungal inoculum as well as a matrix for its storage and handling. Generally, "lignocellulosic substrate" refers to a substrate having lignin, cellulose, or a combination of both lignin and cellulose. In the preferred embodiment the lignocellulosic substrate includes sawdust or wood chips, either alone or in combination, but may also include any substrate that is capable of sustaining the growth of the fungi. Other lignocellulosic substrates may include, without limitation, agricultural residues such as rice straw, corn stalk, wheat straw, etc.

Sawdust or wood chips are preferred, however, for several reasons: (1) they provide a long-term food source for the fungus while providing fungal growth in a wood environment similar to the CCA-treated waste wood environment experienced during inoculation; (2) they permit the production of a large quantity of fungi in a single container; (3) they provide a substrate for easily storing and transporting the fungi; (4) they provide a matrix for convenient and even distribution of the fungus at the inoculation site; and (5) they provide a low cost use of a waste product from saw mills.

The nutrient supplement is defined as a supplement for the lignocellulosic substrate which provides a food source that stimulates rapid and extensive fungal growth beyond that obtained from the lignocellulosic substrate alone. The nutrient supplement may be of any food source which accomplishes the above stated goal and may differ depending upon the fungus selected. Preferably, however, one nutrient supplement used is either a corn steep liquor, cornmeal or wheatbran.

Preferably, the fungal inoculum is prepared by first growing the CCA-tolerant fungus, or fungi, in culture containing malt extract agar. The culture is then typically incubated for one to two weeks, or until a confluent fungal growth is achieved over the agar surface. The incubation is best performed in dark, aerobic conditions, at a relative humidity of about 70%, and at a temperature range from about 20° C. to 35° C., and more preferably at a temperature range from about 27° C. to 32° C.

After achieving a confluent fungal growth, the fungus, lignocellulosic substrate and the nutrient supplement are combined to form the fungal inoculum, or "seeding." The lignocellulosic substrate is first heat-sterilized and allowed to cool. The sterilized lignocellulosic substrate is then mixed with the nutrient supplement and sterile water until a homogenous matrix is formed. The lignocellulosic substrate is preferably combined with the sterile water at 2–3 volumes of water per volume of substrate, while the nutrient supplement is added in a range from about 1% to 5% per volume water. Liquid nutrient supplement should always be added to the sterile water first and solid nutrient supplement should always be mixed with the substrate before adding the sterile water. This will ensure a homogenous matrix.

The homogenous matrix is gently mixed with the fungal culture and allowed to grow to form the final fungal inoculum. The mixture is allowed to grow for a time and under conditions which allow the fungus to reach confluent growth. Preferably, the mixture is grown in dark aerobic conditions, at a relative humidity of about 70%, and in a temperature range from about 20° C. to 35° C., and more preferably at a temperature range from about 27° C. to 32° C. Typically, confluent growth should occur within 4–8 weeks, but depends specifically upon the fungal volume introduced into the matrix, the lignocellulosic substrate, and the nutrient supplement. For example, a heavy fungal inocula with sawdust will shorten the period of fungal growth.

The fungal inoculum is ready for use or storage as soon as it has reached confluent growth. If immediate use is desired, the inoculum can be readily transported to the bioremediation and/or degradation site where it is applied to completely cover the waste wood. In the alternative, if storage is desired, the fungal inoculum can be stored at 4° C. The storage at 4° C. slows the fungal development and prevents overgrowth.

In one preferred embodiment of the present invention, large quantities of industrial inoculum can be produced either with large numbers of tray inoculum, or in large durable plastic bags with aeration patches to allow the appropriate airflow. Trays and bags can be transported easily to the field sites and applied on the waste wood. Production of inoculum directly in the truck or truckload container is also a possibility.

In another embodiment, steam is an alternative source for sterilization. This is especially useful in pilot plants where steam is readily available. In accordance with this embodiment, the steam provides both sterility and moisture content for the lignocellulosic substrate. After being steamed, however, the substrate temperature must be cooled so as to avoid killing the fungi.

Once transported to the bioremediation/degradation site, the fungal inoculum is spread over the waste wood until all of the waste wood is covered. Preferably the waste wood is heat sterilized prior to application so as to minimize other environmental factors which may effect the ability of the fungi to properly degrade or bioremediate the waste wood. Such factors typically include highly competitive bacteria or other fungi.

The CCA-containing waste wood and fungal inoculum mixture is then aerated and hydrated for a time and under conditions sufficient to allow the inoculum to at least partially metabolize the CCA and/or degrade the waste wood to a desired degradation product. The inoculated waste wood is maintained in a dark, aerobic environment, at a relative humidity of about 70%, and in a temperature range from about 20° C. to 35° C., and more preferably in a temperature range from about 27° C. to 32° C. The inoculation environment must have ample air space to ensure proper growth and to allow proper oxygen flow. In the absence of proper oxygen flow fungal growth will be hampered.

The degradation of the wood by the fungal inoculum will generally result in a degradation product having either a reduced volume or a reduced concentration of CCA. Such a product will provide a resource capable of reuse in paper or wood composites, or simply have a reduced volume such that storage or further processing is minimized.

The present invention is further explained by the following examples which should not be construed by ways of limiting the scope or spirit of the present invention.

EXAMPLES

Example 1

Selection of Preservative-Tolerant Fungi

Fungal strains were collected after an extensive screening of the fungal library at the Center for Forest Mycology Research within the U.S. Department of Agriculture, Forest Products Laboratory. The screening process was first initiated by searching the library for fungal strains collected from specific wood products typically treated with wood chemical preservatives, i.e., utility poles, boats, decks, docks and railroad ties. Other strains were isolated from wood samples collected from the field plots of the USDA Forest Services, Forest Products Laboratory in Gulfport, Miss. and from Picnic Point in Madison, Wis. The selected fungal strains were then retrieved and further analyzed to determine their tolerance to CCA, ACQ, creosote and pentachlorophenol.

Chemical preservative tolerance was determined by application of a "choice test." The choice in this case was whether a particular fungal strain would grow towards a wood treated with a chemical preservative or towards a non-treated wood, or both.

To perform the "choice test", a freshly grown fungal malt agar disk (9 mm) was placed in the center of a Petri dish (14 cm diameter) containing 12 ml of water agar, as described in Leithoff et al., "Growth of the copper tolerant ground-rot fungus *Antrodia vaillantii* on different substrates", *The Int'l Research Group on Wood Preservation*, IRG/WP95-10121, incorporated herein by reference. In this particular application, however, no glass ring was applied to the agar disk. A preservative-treated wood sample (1.5 cm×3 cm) was then placed at one edge of the Petri dish while a non-treated wood sample was placed at the opposite edge. The plates were then incubated at 27° C. and 70% relative humidity (RH) for 14 days, wherein fungal growth was monitored.

At the end of 14 days, most fungal strains showed a primary growth preference towards the non-treated wood with no growth towards the treated wood. Some strains, however, showed growth preference towards both directions. Table 1 lists the strains which exhibited the greatest amount of growth towards wood treated with the chemical preservative chromated copper arsenate (CCA). These fungal strains were considered CCA-tolerant and selected for use in later degradation and bioremediation studies.

TABLE 1

Fungi Selected by Choice Test for Tolerance to Preservatives

| Preservative | Strain Name | Isolate Designation | Source |
| --- | --- | --- | --- |
| CCA | Antrodia radiculosa | L-11659-sp | FPL-MC |
| | Glocophyllum subferrugineum | FRI 417/R | FPL-MC |
| | Polyporus sp. | FP134933 | FPL-MC |
| | Trichaptum byssogenum | FP105308-R | FPL-MC |
| | Gloeophyllum trabeum | Boat 228 | FPL-MC |
| | — | TLH-1 | FPL |
| | Antrodia radiculosa | MJL-630 | FPL-MC |
| | Neolentinus lepideus | HHB13625 | FPL-MC |
| | Antrodia xantha | ME268 | FPL-MC |
| | — | CAC-1 | FPL |
| | — | P6G | FPL-pp |
| | — | P71H | FPL-pp |
| | — | UpK | FPL |
| | — | UpL | FPL |
| | Meruliporia incrassata | TFFH-294 | FPL |
| | Meruliporia incrassata | Mad-563 | FPL |
| | Antrodia radiculosa | FP-103272-sp | FPL-MC |
| | Antrodia radiculosa | FP-90848-T | FPL-MC |

FPL-MC: Forest Products Laboratory Center for Forest Mycology Research
FPL: Forest Products Laboratory

Example 2

Determination of Optimum Growth Conditions

The fungal strain *Meruliporia incrassata* (TFFH-294) was used to determine the optimum growth conditions for fungal strains to be used in fungal inocula. Fungal strain *Meruliporia incrassata* (TFFH-294) is a strain that was isolated from the USDA-FS Forest Products Laboratory research plots in Gulfport, Miss.

Optimum Temperature

Four temperature settings, 20, 27, 32 and 37° C. were studied to determine their effect on fungal growth. Four disks of fungal culture were inoculated onto malt extract liquid medium (Difco Bacto malt extract). After incubation for 12 days at the various temperatures, the mycelia of the fungi were harvested on Whatman No.1 filter paper, air dried and measured for biomass dry weight.

The results showed that the optimal temperature for fungal growth was in a range between about 27° C. and 32° C. Incubation at a higher temperature setting of 35° C. showed a substantial decline in growth, as did incubation at a lower temperature setting of 20° C.

Optimal Light Conditions

Light effect on growth was studied under three settings, 24 hours of light, 12 hours of light with 12 hours of darkness, and 24 hours of darkness. Fungal inoculant was grown in malt extract liquid medium as above for a period of 21 days. Mycelia were then harvested, air dried and weighed to obtain biomass measurements.

The results of light effect are shown in Table 2. Fungi produced more cell mass under the complete dark growth condition than under either a mixture of light/dark or complete light. Cell mass measurements increased 33% at 24 hours dark cycle then at 24 hours light cycle.

TABLE 2

Light Effect on TFFH-294 Growth

| Light condition | Dry Weights, Mg (±S.D.) |
|---|---|
| 24 hours of light | 66 ± 8 |
| 12 hours of light/dark | 70 ± 6 |
| 24 hours of dark | 88 ± 13 |

Defined Liquid Medium

Fungal cultures were inoculated in Bailey media (Bailey et al., "Cellulase (B-1,4-Gucan,4-Glucanohydrolase) from Wood-Degrading Fungus Polyporus Chweinitzii," *Fr. I. Purification Biochem. Biophys. Acta,* 185:381–391 (1969)), and BIII media (Kirk et al., "Production of Multiple Ligninases by *Phanerochaete chrysosporium:* Effect of Selected Growth Conditions and Use of a Mutant Strain," *Enzyme Microb. Technol.,* 8:27–32 (1986)) to determine which medium provided better fungal growth. Fresh fungal cultures were grown on malt extract agar plates. Four agar discs (9 mm) of complete fungal growth were removed and inoculated into 25 ml growth medium in 125 ml flasks. Two flasks were then kept stationary at 27° C. and 70% RH for 21 days. After 21 days, the mycelia were harvested for biomass measurements.

The biomass measurements indicated that the biomass growth for TFFH 294 was better in Bailey medium over BIII medium. The Bailey medium produced an average dry weight mass of 20 mg±10 mg, while the BiII medium produced an average dry weight mass of 16 mg±5 mg. It is understood, however, that certain types of fungi may grow better in certain types of media. Accordingly, the limitation of the present invention to one type of media over another is not necessary.

Oxygen

Fungal cultures were grown with or without oxygen-enhancement, i.e., oxygen flush, to determine the effects of oxygen upon fungal growth. Fungal cultures were inoculated in Bailey media or Bill media, and grown on malt extract agar plates. From the plates, four agar disks (9 mm) of complete fungal growth were removed and inoculated into 25-ml growth medium in 125-ml flasks. The flasks were grown with and without oxygen flush, and were kept stationary at 27° C. and 70% RH for 21 days. Oxygen-enhanced cultures were flushed with oxygen every other day for an interval of 20 seconds. After 21 days, the fungal mycelia were harvested, air dried and measure for dry weight.

From the mycelia dry weight measurements, the results showed that oxygen-enhanced incubation provided fungal growth similar to that of the white-rot fungi, *Phanaerochytes chrysoporium* (Kirk et al. 1986). As seen in Table 3 below, the enhanced growth effect has consequently produced a lower pH value in the culture flasks, thus indicating confluent growth.

TABLE 3

Oxygen Effect on Fungal Growth with Two Defined Media

| Strain | Medium | $O_2$ | Dry weights, mg (±S.D.) | pH |
|---|---|---|---|---|
| TFFH 294 | Bailey | + | 23 ± 1 | 2.73 |
|  |  | − | 20 ± 1 | 3.04 |
|  | BIII | + | 21 ± 2 | 2.96 |
|  |  | − | 18 ± 2 | 3.61 |

Example 3

Nutrient Supplements: Corn Steep Liquor

Fungal inoculum containing *Meruliporia incrassata* (TFFH-294) was added to malt extract liquid media supplemented with 1, 2.5 and 5% of sterile corn steep liquor (CSL) (ADM corn processing, Cedar Rapids, Iowa). Media containing no CSL was used as a control. Cultures were grown at 27° C. and 70% RH for 30 days. After 30 days, Mycelium was separated from liquid culture by filtration, oven dried and weighed. The % dry weight was determined as a percent of the dry weight for the inoculum without CSL.

The addition of the corn steep liquor to the growth medium had a profound effect on fungal growth. Various concentrations of CSL were tested and results are shown in Table 4 below. The highest enhancement effect was obtained by adding 1% CSL in malt extract medium. This enhancement should limit the disadvantage experienced by various fungal strains, such as TFFH-294, which are typically disadvantaged by their slow growth characteristic that limits their competition with other dominant fungi in nature, such as *Postia placenta* and *Gloeophyllum trabeum.* Accordingly, the supplementation with a CSL nutrient will allow better competition in nature.

TABLE 4

Effect of CSL on TFFH-294 Growth

| CSL concentration | % Dry weight gain |
|---|---|
| 0 | 100 |
| 1.0% | 321 |
| 2.5% | 256 |
| 5.0% | 196 |

Example 4

Effect of Corn Steep Liquor on Fungal Growth for Fungi Tolerant to Different Wood Chemical Preservatives Fungal inoculum containing fungal strains exhibiting tolerance to either CCA, ACQ, creosote or pentachlorophenol were supplemented with 1% sterile CSL (ADM corn processing, Cedar Rapids, Iowa) in malt extract media to determine the effect of the CSL on the growth patterns of the separate strains. Media without CSL was used as a control and considered to exhibit 100% growth. Weight was determined from fungal mycelia incubated for 3 weeks in liquid malt extract, with or without CSL, at 27° C. and 70% RH. After 3 weeks, the mycelia was removed from the liquid by filtration on filter paper, oven dried and weighed. The % dry weight was determined as percent of the dry weight for the inoculum without CSL. Table 5 illustrates the increase growth effect that the CSL provides to the various strains used.

TABLE 5

Effect of corn steep liquor (CSL) on fungal growth in liquid medium.

| Strain* | CSL | Net weight (g)^ | % growth^^ |
|---|---|---|---|
| TFFH-294 | − | 0.053 ± 0.011 | 100 |
|  | + | 0.108 ± 0.027 | 203 |
| FP-90848-T | − | 0.079 ± 0.013 | 100 |
|  | + | 0.116 ± 0.023 | 147 |
| Mad-534 | − | 0.049 ± 0.004 | 100 |
|  | + | 0.114 ± 0.006 | 233 |
| Mad-617 | − | 0.028 ± 0.003 | 100 |
|  | + | 0.106 ± 0.022 | 379 |
| FP-103272-sp | − | 0.058 ± 0.009 | 100 |
|  | + | 0.114 ± 0.017 | 196 |

*TFFH-294 and FP-90848-T are CCA-tolerant and ACQ-tolerant; Mad-534 and Mad-617 are creosote-tolerant; and FP-103272-sp is penta-tolerant and creasote-tolerant.
^Weight determined from fungal mycelia incubated for 3 weeks in liquid malt extract, with or without cornstarch liquor (CSL), removed from liquid by filtration on filter paper, oven dried and weighed.
^^Medium without CSL (−) is the control, with 100% growth. Growth of medium with CSL (+) is expressed as % control.

Degradation of the treated wood block was observed by placing the sterile block on the surface of the fungal inoculum in the glass bottle. Fungi strains known to be tolerant to a specific preservative were exposed to blocks having their respective preservative. The blocks were then incubated for 10 weeks at 27° C. and 70% RH. After 10 weeks, the remaining portion of the blocks were removed and their dry weight loss was measured according to ASTM standards.

Table 6 below depicts the ability of the fungal inoculum having certain fungal strains to degrade the preservative-treated wood. As can be seen the fungal strains of *Meruliporia incrassata* (TFFH-294), *Antrodia radiculosa* (MJL-630), *Meruliporia incrassata* (Mad-563) and *Antrodia radiculosa* (FP-90848-T) were able to degrade the CCA-treated wood at an average of greater than 20% of the original dry weight of the wood. *Antrodia radiculosa* (FP-90848-T) was also able to degrade ACQ-treated wood at an average of 29.9% of the original dry weight. *Antrodia radiculosa* strains FP-103272-sp, L-11659-sp, and FP-90848-T, and *Meruliporia incrassata* (Mad-563) were able to degrade on average approximately 3% of the wood block having a concentration of Pentachlorophenol. Finally, *Antrodia radiculosa* strains FP-103272-sp, L-11659-sp, and FP-10539-R, and *Neolentinus lepideus* (Mad-534) exhibited the ability to reduce the dry weight of wood having creosote by an average of approximately 3%.

TABLE 6

Fungal Degradation of Preservative-Treated Wood*

| Fungus | UNTREATED | | ACQ | | CCA | | Penta | | Creosote | |
|---|---|---|---|---|---|---|---|---|---|---|
|  | Avg | SD | Avg | SD | Avg | SD | Avg | SD | Avg | SD |
| *Meruliporia incrassata* (TFFH-294) | 62.2 | 2.9 | 9.7 | 5.7 | 36.8 | 2.7 | 1.9 | 0.3 | 1.8 | 0.2 |
| *Antrodia radiculosa* (MJL-630) | 32.6 | 4.8 | 6.7 | 6.8 | 26.6 | 2.9 | 1.5 | 0.1 | 1.7 | 0.2 |
| *Meruliporia incrassata* (Mad-563) | 62.5 | 2.5 | 3.5 | 0.1 | 23.7 | 7 | 4.1 | 2.5 | 1.5 | 0 |
| *Antrodia radiculosa* (FP-90848-T) | 39.5 | 4.1 | 29.9 | 14.3 | 20.1 | 7.7 | 2.6 | 0.5 | 2.1 | 0.2 |
| *Antrodia radiculosa* (FP-103272-sp) | 24.6 | 6 | 0.7 | 0.1 | 6.5 | 4.7 | 4.7 | 2.3 | 5.5 | 2 |
| *Antrodia radiculosa* (FP-105309-R) | 27.2 | 3 | 4.4 | 4 | 2.3 | 0.8 | 2.4 | 0.6 | 2.9 | 0.8 |
| *Antrodia radiculosa* (L-11659-sp) | 23.1 | 2.7 | 0.8 | 0.3 | 1.3 | 1.3 | 5.3 | 1.8 | 3.2 | 1.8 |
| *Neolentinus lepideus* (Mad-534) | 38.8 | 5.3 | 1.4 | 0.3 | −0.7 | 0.4 | 1.5 | 0.1 | 4.1 | 0.7 |

*Standard Method of Testing Wood Preservatives by Laboratory Soil-Block Cultures, ASTM D-1413-76

Example 5

Preservative Wood Degradation Study

A degradation study was performed using fungal strains exhibiting tolerance to either CCA, ACQ, creosote or pentachlorophenol. Blocks of wood were cut (1×1×0.3 inches) from southern pine (*Pinus* sp.) and treated to CCA, ACQ, creosote and pentachlorophenol according to American Wood Preserver's Association (AWPA) standards ("American Wood Preserver's Association: Book of Standards," American Wood-Preserver's Association, Woodstock, Md., 1991). The blocks of wood were sterilized and allowed to cool.

Effect of Additives on Degradation of Preservative-Treated Wood

A study was also performed to determine what effect the additives had on the ability of certain fungal strains to degrade preservative-treated wood. A fungal inoculum was prepared for each stain using one of the selected fungi as described above. First, the fungus was grown on 10 ml malt extract agar in a glass bottle (2×2×5 h inches) and incubated at 27° C., 70% RH, for 1–2 weeks until a confluent growth on the agar layer occurred. A mixture of soft wood and hard wood sawdust was sterilized and set for use as a lignocellulosic substrate.

Separate fungal inocula were prepared containing a nutrient supplement of either corn steep liquor or cornmeal and wheatbran. For the inoculum containing corn steep liquor, 10 g of the sterile sawdust was mixed with 20 ml of sterile water containing 1% commercial corn steep liquor (v/v) and added to the glass bottle containing the fungal growth. For the inoculum containing cornmeal and wheat bran, 10 g of the sterile sawdust was combined with the corn meal and wheat bran at 2.5% (w/w, 0.25 g corn meal or wheat bran/10 g sawdust) for each ingredient, followed by 20 ml of sterile water. The inoculum was then added to another glass bottle containing the fungal growth. Incubation was continued in a stationary condition and at a temperature of 27° C. and 70% RH. The length of incubation depended on the rate of fungal growth, however, after about 4–6 weeks of incubation fungal mycelia growth was obvious. The fungal strains utilized are those depicted in table 7. These results indicate that additives enhance degradation of preservative-treated wood.

ber degradation study. A 2 inch layer of moistened soil having a water content of 35% was placed in the degradation chamber. Formed pieces of 12 inch cut CCA-treated 2×4 lumber was pieced on top of the soil and the metal degradation chambers were sterilized in an autoclave. After the chambers had cooled down to room temperature, the TFFH-294 fungal chips inoculum was poured onto the preservative-treated lumber until the lumber was completely covered. The chamber containing the inoculated lumber was then stored at 27° C. and 70% RH for 12 weeks. At the end of the 12 week incubation period the wood was harvested and measured for dry weight loss to determine the level of degradation. Results showed a 28% degradation of CCA-treated wood as compared to nontreated control wood.

While the present invention has now been described and exemplified with some specificity, those skilled in the art

TABLE 7

Effect of additives to degradation of preservative-treated wood.

| CHEMICAL | FUNGAL SPECIES | ISOLATE # | WEIGHT* | cmwb** | CSL*** | SYP**** |
|---|---|---|---|---|---|---|
| CCA | *Antrodia radiculosa* | L-11659-sp | 32.0 mg | 150% | 446% | 972% |
|  | *Polyporus* sp | FP134933 | 12.3 mg | 1040% | 577% | 1284% |
|  | (unknown) | F43G | 1.0 mg | 3500% | 500% | 114% |
|  | *Diplomitoporus lindbladii* | FP134600 | 13.0 mg | 469% | 238% | 753% |
|  | *Meruliporia incrassata* | TFFH-294 | 34.0 mg | 32% | 208% | 179% |
| ACQ | Chain *chlamydospore* | ME681 | 27.0 mg | 63% | 56% | 248% |
|  | *Antrodia radiculosa* | FP-90848-T | 17.0 mg | 176% | 188% | 243% |
|  | — | UpK | 38.0 mg | 118% | 103% | 34% |
|  | — | UpL | 50.0 mg | 82% | 120% | 678% |
| Creosote | *Gloeophyllum Subferrugineum* | FPL 508 | 64.0 mg |  | 103% | 39% |
|  | *Melanoporia niger* | MD278 | 66.0 mg | 95% | 127% | 772% |
|  | — | UpK | 51.0 mg | 112% | 110% | 14% |
|  | *Polyporus* sp. | FP101605 | 61.0 mg | 101% | 111% | 224% |

*Weight of preservative-treated pine sawdust. Control weight. Growth is based on % of control weight.
**% growth on pine sawdust amended with cornmeal (cm) and wheatbran (wb)
***% growth on pine sawdust amended with cornstarch liquor (SCL)
****SYP = Southern yellow pine sawdust with no preservatives.

Example 6

Scale-up of Fungal Inoculum in Laboratory

Fungal Culture Preparation

Five to seven Petri dishes (14 cm diameter) containing malt agar were used to grow fungal inoculum containing the fungal strain *Meruliporia incrassata* (TFFH-294). The Petri dishes were incubated at 27° C. and 70% RH until a confluent growth occurred on the agar layer. Agar chunks of 1–1.5 inches square were removed and immediately transferred to the solid substrate matrix already prepared as described below.

Solid Substrate Matrix in Tray

Solid substrate comprising a lignocellulosic substrate and nutrient supplement were prepared in an aluminum tray (9×13×2.5 h inches). First, 350 gm of sawdust was placed in the empty tray and the tray and sawdust autoclaved and cooled to room temperature. Once the tray and sawdust was cooled, 700 ml of sterile water having a 1% concentration of corn steep liquor was added and mixed to achieve a homogenous solid matrix. The fungal squares were then gently mixed with the solid matrix, covered with foil and incubated. Incubation was in dark conditions and at 27° C., 70% RH, for a period of 4–8 weeks, or until confluent growth was obtained. After the fungus had reached confluent growth, the fungal inoculum was stored at 4° C. to prevent overgrowth.

Preservative Lumber Degradation in Degradation Chamber

Several large metal degradation chambers (33×6×8 h inches) with sliding covers were custom-made for the lumwill appreciate the various modifications, including variations, additions, and omissions, that may be made in what has been described. Accordingly, it is intended that these modifications also be encompassed by the present invention and that the scope of the present invention be limited solely by the broadest interpretation that lawfully can be accorded the appended claim.

We claim:

1. A method for bioremediating wood containing chromated copper arsenate (CCA) comprising the steps of:
   inoculating wood containing CCA with a fungal culture comprising at least one CCA-tolerant fungus selected from the group consisting of *Meruliporia incrassata* (TFFH-294) and *Antrodia radiculosa* (MJL-630), at least one lignocellulosic substrate and at least one nutrient supplement, the lignocellulosic substrate and the nutrient supplement in an amount sufficient to produce a biomass of the fungal culture sufficient to at least partially remediate the CCA; and
   aerating and hydrating the inoculated wood for a time and under conditions sufficient to allow the fungal culture to remediate the CCA.

2. The method of claim 1 wherein the CCA tolerant fungus is *Meruliporia incrassata* (TFFH-294).

3. The method of claim 1 wherein the lignocellulosic substrate is selected from the group consisting of sawdust, wood chips, rice straw, corn stalks, and wheat straw.

4. The method of claim 1 wherein the nutrient supplement is selected from the group consisting of corn steep liquor, cornmeal and wheatbran.

5. The method of claim 1 wherein the inoculated wood is aerated and hydrated in dark, aerobic conditions, at a relative humidity of about 70%, and in a temperature range from about 20° C. to 35° C.

6. The method of claim 5 wherein the inoculated wood is aerated and hydrated in a temperature range from about 27° C. to 32° C.

7. A method for degrading wood containing chromated copper arsenate (CCA) comprising the steps of:

inoculating wood containing CCA with a fungal culture comprising at least one CCA-tolerant fungus selected from the group consisting of *Meruliporia incrassata* (TFFH-294) and *Antrodia radiculosa* (MJL-630), at least one lignocellulosic substrate and at least one nutrient supplement, the lignocellulosic substrate and the nutrient supplement in an amount sufficient to produce a biomass of the fungal culture sufficient to degrade the wood; and aerating and hydrating the inoculated wood for a time and under conditions sufficient to allow the fungal culture to degrade the wood to reach a degradation product.

8. The method of claim 7 wherein the CCA-tolerant fungus is *Meruliporia incrassata* (TFFH-294).

9. The method of claim 7 wherein the lignocellulosic substrate is selected from the group consisting of sawdust, wood chips, rice straw, corn stalks, and wheat straw.

10. The method of claim 7 wherein the nutrient supplement is selected from the group consisting of corn steep liquor, cornmeal and wheatbran.

11. The method of claim 7 wherein the inoculated wood is aerated and hydrated in dark, aerobic conditions, at a relative humidity of about 70%, and in a temperature range from about 20° C. to 35° C.

12. The method of claim 11 wherein the inoculated wood is aerated and hydrated in a temperature range from about 27° C. to 32° C.

13. The method of claim 7, wherein the degradation product exhibits a loss in dry weight of an amount in excess of 20% of the dry weight of the wood.

14. A method for preparing a fungal culture for degrading or bioremediating wood containing chromated copper arsenate (CCA), comprising the steps of:

combining at least one CCA-tolerant fungus selected from the group consisting of *Meruliporia incrassata* (TFFH-294) and *Antrodia radiculosa* (MJL-630) with a matrix comprising at least one lignocellulosic substrate, at least one nutrient supplement, and sterile water; and growing the CCA-tolerant fungus and matrix combination in dark, aerobic conditions, at a relative humidity of about 70%, and in a temperature range of about 20° C. to 35° C.

15. The method of claim 14 wherein the CCA-tolerant fungus and matrix combination is grown in a temperature range of about 25° C. to 32° C.

16. The method of claim 14 wherein the volume of lignocellulosic substrate is about 25% to 33% the volume of sterile water, and the volume of nutrient supplement is about 1% to 5% the volume of sterile water.

* * * * *